United States Patent [19]
Cunningham et al.

[11] Patent Number: 5,601,775
[45] Date of Patent: Feb. 11, 1997

[54] PROCESS FOR MAKING AN ABRASION RESISTANT QUASI MONOFILAMENT

[75] Inventors: David V. Cunningham, Midlothian, Va.; Sheldon Kavesh, Whippany, N.J.; Christopher P. Griffin, Chester, Va.; Allan R. Hall, West Warwick, R.I.

[73] Assignee: AlliedSignal Inc., Morristown, N.J.

[21] Appl. No.: 410,534

[22] Filed: Mar. 24, 1995

[51] Int. Cl.$^6$ .............. B29C 47/02; D02G 3/36
[52] U.S. Cl. .......... 264/469; 264/103; 264/129; 264/134; 264/171.13; 264/171.23; 264/210.8
[58] Field of Search .................. 264/103, 129, 264/134, 171.13, 171.23, 210.8, 211.14, 469

[56] References Cited

U.S. PATENT DOCUMENTS

| | | | |
|---|---|---|---|
| 3,551,280 | 12/1970 | Kippan | 264/171.23 X |
| 4,050,230 | 9/1977 | Senoo et al. | 57/231 |
| 4,202,164 | 5/1980 | Simpson et al. | 57/232 |
| 4,275,117 | 6/1981 | Crandall | 428/373 |
| 4,297,413 | 10/1981 | Sasaki et al. | 428/394 |
| 4,403,012 | 9/1983 | Harpell et al. | 428/290 |
| 4,413,110 | 11/1983 | Kavesh et al. | 526/348.1 |
| 4,422,993 | 12/1983 | Smith et al. | 264/210.8 |
| 4,430,383 | 2/1984 | Smith et al. | 428/364 |
| 4,436,689 | 3/1984 | Smith et al. | 264/204 |
| 4,501,856 | 2/1985 | Harpell et al. | 525/240 |
| 4,536,536 | 8/1985 | Kavesh et al. | 524/462 |
| 4,543,286 | 9/1985 | Harpell et al. | 428/288 |
| 4,545,950 | 10/1985 | Motooka et al. | 264/210.6 |
| 4,551,296 | 11/1985 | Kavesh et al. | 264/203 |
| 4,563,392 | 1/1986 | Harpell et al. | 428/394 |
| 4,584,240 | 4/1986 | Herbert et al. | 428/373 |
| 4,894,195 | 1/1990 | Wang | 264/134 |
| 4,916,000 | 4/1990 | Li et al. | 428/105 |
| 5,180,636 | 1/1993 | Harazoe et al. | 428/373 |
| 5,277,974 | 1/1994 | Kubo et al. | 428/373 |

FOREIGN PATENT DOCUMENTS

| | | |
|---|---|---|
| 0205960 | 12/1986 | European Pat. Off. |
| 6-22666 | 2/1994 | Japan |

Primary Examiner—Leo B. Tentoni
Attorney, Agent, or Firm—Renee J. Pymarz; Melanie L. Brown

[57] ABSTRACT

A quasi monofilament having a high strength polyethylene fiber core with an adherent, abrasion resistant polymer sheath is prepared by feeding the core yarn through a crosshead die, while simultaneously supplying a polymer melt at a temperature greater than the melting point of the core yarn to the die, for sheathing the core yarn within the die with the melt under a sufficient pressure to cause the melt to adhere to the core yarn. The abrasion resistant polymer sheath includes an effective amount of a first polymer having ethylene crystallinity, a density of at least about 0.94 g/cm$^3$, and a melt index of less than about 0.1 g/10 min. The composition used to sheathe the core yarn is characterized by a weight average tensile strength at yield of greater than about 13.8 MPa. The quasi monofilament has utility in applications subjected to high abrasion, such as sports fishing lines, kite lines, dental floss, "weedeater" lines and tennis racket strings.

22 Claims, 2 Drawing Sheets

PROCESS FOR MAKING AN ABRASION RESISTANT QUASI MONOFILAMENT

BACKGROUND OF THE INVENTION

1. Field of the Invention

The present invention relates to a process for making an abrasion resistant quasi monofilament having a high strength polyethylene fiber core with an adherent, abrasion resistant polymer sheath. More particularly, this invention relates to a process for making such a quasi monofilament by crosshead pressure extrusion sheathing at a temperature above the melting point of the core fibers.

2. Prior Art

Polyethylene yarns having very high tenacity have previously been described in U.S. Pat. Nos. 4,413,110, 4,430, 383, 4,436,689, 4,536,536, and 4,545,950. The nature of the spinning processes used to prepare these yarns is such that individual filaments are typically of low denier and consequently break at low applied loads. To remedy this, multi-filament yarns may be used or several multi-filament yarns may be formed into a braid. However, such multi-filament yarns or braids are "limp", i.e., they have little flexural rigidity, and consequently bend easily when subjected to a transverse force. Additionally, in applications subjected to high abrasion, the individual low denier filaments of the multi-filament yarns may be rapidly worn through to produce debris or fibrillations which can snag or otherwise compromise the utility of the yarn or braid. In such applications it would therefore be highly desirable to have an article of high tenacity and high denier possessing high absolute breaking load together with flexural rigidity and high abrasion resistance. Examples of such applications are sports fishing lines, kite lines, dental floss, "weedeater" lines and tennis racket strings.

High strength polyethylene fibers or yarns coated with polyethylene or in a polyethylene matrix material are known. U.S. Pat. No. 4,501,856 discloses a composite of high strength polyethylene fibers in a matrix material which "may be any of the various known forms of polyethylene, including low density polyethylene (density of between 0.90 and 0.94 g/cm$^3$), high density (between 0.94 and 0.98 g/cm$^3$), linear low density or other conventional forms." U.S. Pat. Nos. 4,543,386 and 4,563,392 describe composites wherein high strength polyethylene fibers are coated on at least a portion of their surface with a solution of high density or low density polyethylene. U.S. Pat. Nos. 4,403,012 and 4,916,000 also mention coating high strength polyethylene fibers with polyethylene. JP-A-6022666 describes the preparation of fishing line which is composed of ultrahigh molecular weight polyethylene fibers which have been dipped in polyethylene wax at less than 90° C.

The extrusion coating of aramid fiber bundles or ropes with polyethylene is also known. U.S. Pat. No. 4,202,164 describes a thermoplastic coated aramid rope wherein the coating can be polyethylene extruded under pressure into the interstices of the rope. U.S. Pat. No. 4,050,230 describes covering an uncured, thermosetting resin-coated bundle of aramid or glass fibers with molten polyethylene, for example by extrusion coating with the melt at a temperature of 200° C. and under vacuum.

None of these publications, however, describes a process of crosshead pressure extrusion sheathing a high strength fiber core at a temperature above the melting point of the core fibers. These documents also fail to describe the use of a sheathing composition comprising as a critical component thereof a polymer having ethylene crystallinity, a density of at least 0.94 g/cm$^3$, and a melt index of less than about 0.1 g/10 min.

SUMMARY OF THE INVENTION

The present invention is a process for making an abrasion resistant quasi monofilament. This process comprises the steps of:

a. continuously feeding a core polyethylene multi-filament yarn having a tenacity of at least about 15 g/d and a tensile modulus of at least about 500 g/d through a crosshead die, while simultaneously b. supplying a polymer melt at a temperature greater than the melting point of the core yarn to the die, for c. sheathing the core yarn within the die with the melt under a sufficient pressure to cause the melt to adhere to the core yarn; and d. cooling the sheathed yarn to below the melting point of the polymer melt.

The process may additionally comprise the optional steps of: twisting the core yarn prior to the feeding step; pretreating the core yarn, preferably after twisting, to enhance adherence of the melt to the core yarn; stretching the core yarn simultaneous with the sheathing step; and/or post-stretching the sheathed core yarn. Post-stretching is conducted as described in EP 205,960B at a temperature within about 10° C. of the melting point of the core yarn, at a stretch rate of less than about 1 sec$^{-1}$, and the post-stretched sheathed yarn is cooled under tension sufficient to retain the highly oriented state of the core yarn. In a preferred embodiment, the process additionally comprises the twisting step. The present invention also includes the quasi monofilaments produced by the processes of this invention.

There is provided by the process of the present invention a quasi monofilament of indefinite length comprising (a) a core of polyethylene multi-filament yarn having a tenacity of at least about 15 grams per denier (g/d) and a tensile modulus of at least about 500 g/d; and adhered thereto (b) an abrasion resistant sheath comprising an effective amount of a first polymer having ethylene crystallinity, a density of at least about 0.94 g/cm$^3$ and a melt index of less than about 0.1 g/10 min. The sheath preferably also comprises an effective amount of a compatible processing aid. The preferred sheathing composition is characterized by a weight average tensile strength at yield of greater than about 13.8 MPa.

The quasi monofilament made in accordance with this invention is a unique and useful article possessing the high tensile properties and low elongation of the core yarn combined with the flexural rigidity of a monofilament. It is particularly advantageous as sports fishing line and in numerous other applications.

BRIEF DESCRIPTION OF THE DRAWINGS

The invention will be more fully understood and further advantages will become apparent when reference is made to the following detailed description of the invention and the accompanying drawings in which.

DESCRIPTION OF THE PREFERRED EMBODIMENTS

By "quasi monofilament" is meant an article which has the look and feel of a monofilament, i.e., a single untwisted synthetic filament, but which actually comprises a sheathed multi-filament core yarn, which may have been twisted prior to sheathing.

The present invention produces a quasi monofilament of indefinite length comprising (a) a core of polyethylene multi-filament yarn of very high tenacity and tensile modulus and (b) an adherent, abrasion resistant sheath of a polymeric material deposited on the core by a process of crosshead pressure extrusion at melt temperatures in excess of the melting point of the core yarn. This structure is new, novel and useful.

Preferably, the core yarn consists of polyethylene filaments having a weight average molecular weight in excess of about 300,000 kg/kg-mole, a tenacity of at least about 15 g/d, and a tensile modulus of at least about 500 g/d. The intrinsic viscosity of the core yarn may be about 3 to about 29 dl/g as measured in decalin at 135° C., more preferably about 7 to about 15 dl/g. The core yarn of this invention can be made by the method of U.S. Pat. Nos. 4,551,296 or 4,413,110 or by the methods described in EP 205 960B, all of which are hereby incorporated by reference. Tensile properties referred to have in are determined through utilization of an Instron tensile tester using a 10 inch gauge length and a stain rate of 100 percent per minute, in accordance with ASTM D2256.

The polyethylene core yarn may be composed of from about 5 to about 9600 individual filaments of about 0.5 to about 20 denier/filament (dpf). More preferably, the core yarn is composed of from about 30 to about 400 filaments of about 1 to 10 dpf. The core yarn may be twisted or untwisted, but preferably is twisted with about 0.1 to about 20 turns/inch (tpi), more preferably with about 0.5 to about 15 tpi, the lower twist count being used for higher yarn deniers and the higher twist count being used for lower yarn deniers.

The sheathing composition can be any polymeric material that exhibits satisfactory adhesion to the core yarn and resistance to abrasion in accordance with Federal Motor Vehicle Safety Standard 209, modified as follows. The quasi monofilament to be tested for adhesion and abrasion resistance is clamped at one end and subjected to a reciprocating motion in a horizontal direction over a distance of 32 cm at a frequency of 0.5 Hz. To the other end of the line is suspended a 1 oz. weight. At a point between the two ends of the line, it passes through and bears against a fishing rod guide ("Hardloy" silicon carbide guide by Fuji) of 8 mm diameter. As the line passes through the guide, the direction of the line is changed from horizontal to vertical. At the completion of 2500 cycles of reciprocating motion against the fishing rod guide, the line is detached from the apparatus and visually examined for signs of abrasion or detachment of the sheath from the core. If there are no signs of detachment, the adhesion/abrasion property of the sheath is rated as "satisfactory". If abrasion has exposed areas of the core yarn, the adhesion/abrasion property of the sheath is rated as "unsatisfactory."

Preferably, the sheathing composition possesses a weight average tensile strength at yield in excess of about 13.8 MPa by application of the rule of mixtures to its components. By "weight average tensile strength at yield" is meant the sum of the products of the weight fractions and tensile strengths of each of the components. The tensile strength at yield of the individual components is measured by ASTM Standard D638. Higher weight average tensile strengths of the sheathing composition and higher twist levels of the core fibers are preferred so as to provide greater flexural rigidity and also to reduce flattening of the article in the fishing line application caused by bearing against the fishing pole guides. Preferably the sheathing composition comprises a polyolefin, polyolefin copolymer or polyolefin blend. Components of the sheath may include, but are not limited to, high density polyethylene, low density polyethylene, linear low density polyethylene, ethylene copolymers with non-olefinic monomers, ethylene-propylene copolymer, polyethylene wax, antioxidant, colorant and ultraviolet light stabilizer.

The sheathing composition preferably includes a processing aid in combination with an effective amount of a first polymer having ethylene crystallinity, a density of at least about 0.94 g/cm$^3$ as measured by ASTM D972, and a melt index of less than about 0.1 g/10 min as measured by ASTM D1238 at condition 190° C./2.16 kg. The Comparative Examples which follow will show that using polymers having a density of less than about 0.94 g/cm$^3$ and a melt index of greater than about 0.1 g/10 min for the first sheath polymer produces sheathed yarns having poor adhesion and abrasion resistance. The processing aid has the effect of increasing the flow of the first sheath polymer. The choice of processing aid is not critical so long as its melting point is below the processing temperature, its melt index is greater than that of the first sheath polymer, and it is thermally stable at the processing temperature. A processing aid meeting these characteristics is deemed compatible with the first sheath polymer. Suitable processing aids may include polymers having ethylene crystallinity and a melt index exceeding about 1 g/10 min, as well as waxes.

In a preferred embodiment, the sheathing composition is a blend which includes about 15 to about 95, more preferably about 25 to about 75, weight percent of the first polymer as defined above, which is preferably polyethylene. The blend further comprises, as a processing aid, about 5 to about 85, more preferably about 25 to about 75, weight percent of a polymer having ethylene crystallinity, a melt index exceeding about 1 g/10 min and a density of greater than about 0.94 g/cm$^3$. The preferred melt index for the second polymer ranges from about 1 to about 100 g/10 min. The sheathing composition optionally comprises about 1 to about 20 weight percent, more preferably about 2 to about 10, weight percent of a processing aid consisting of a wax, preferably polyethylene wax. The polyethylene wax has a density of at least about 0.92 g/cm$^3$ and a viscosity at 140° C. of at least about 50 cps Brookfield viscosity. All weight percents are on the weight of the blend. Blends of blends can also be used.

The sheath should form about 10 to about 90 weight percent of the quasi monofilament article, the proportion to be determined in relation to the end-use application. For fishing line, the sheath preferably forms about 15 to about 60 weight percent of the quasi monofilament article, and most preferably about 20 to about 45 weight percent.

The process of the present invention by which the described product is made minimally comprises the following steps: (a) continuously feeding the core polyethylene multi-filament yarn through a crosshead die, while simultaneously (b) supplying a polymer melt at a temperature greater than the melting point of the core yarn to the die, for (c) sheathing the core yarn within the die with the melt under a sufficient pressure to cause the melt to adhere to the core yarn; and (d) cooling the sheathed yarn to below the melting point of the polymer melt. These process steps and associated conditions will be described in detail below. There are also several optional process steps. These steps include twisting the core yarn prior to the feeding step; pretreating the core yarn, preferably after twisting, to enhance adherence of the melt to the core yarn; stretching the core yarn simultaneous with the sheathing step; and/or post-stretching the sheathed core yarn at a temperature within about 10° C. of the melting point of the core yarn at a stretch rate of less than about 1 sec$^{-1}$ and cooling under tension sufficient to maintain the high orientation of the core yarn. The preferred process will depend upon the application; with sports fishing lines, the preferred process includes the optional step of twisting.

Figure 1:
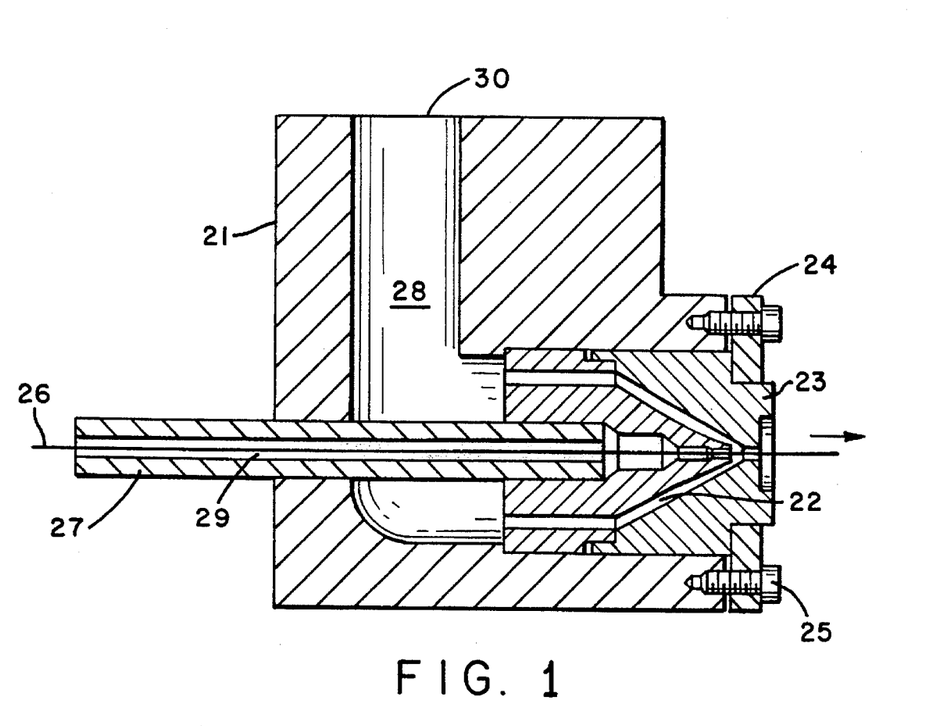
FIG. 1 is a top view in section of apparatus used in Comparative Examples 19 through 27 and in Examples 28 through 55 of the invention.

The quasi monofilament article can be made by contacting the core yarn with the desired sheath material where the sheath material is in a melt state. Advantageously, the core yarn is withdrawn from a supply source and continuously fed through a melt of the sheath material in a crosshead pressure extrusion die where it is sheathed. From the die, the sheathed yarn travels through a cooling zone to be taken up. A crosshead pressure extrusion die is also known as a wire-coating pressure die. A description of such a die is to be found in the Encyclopedia of Polymer Science and Engineering, Vol. 11, p.273, John Wiley & Sons, New York, 1988. In FIG. 1, die 23 is held in place against crosshead die body 21 with die retaining ring 24 and associated bolt 25. Crosshead die body 21 has a melt feed channel 28 therein, characterized, as is typical of crosshead dies, by a 90 degree bend. Core tube 27 and associated guider tip 22, which have an axial bore 29 for passage of core yarn 26 therethrough, are mounted within crosshead die body 21 so as to define an annular melt delivery channel at the exit end of guider tip 22. The exit end of guider tip 22 is within die 23.

Core yarn 26 enters axial bore 29 of core tube 27 and exits from guider tip 22 (left to right in the drawing figure). The melt, supplied by an extruder (not shown) to melt delivery channel 28 through entrance 30, flows around the 90 degree bend into the annular melt delivery channel to contact moving yarn 26 at the exit end of guider tip 22 inside die 23. The melt sticks to and is pulled by moving yarn 26 to sheathe the core yarn 26. From the exit of die 23, the sheathed yarn passes through an air gap to a water bath (not shown) where it is cooled to below the melting point of the polymer melt. From the water bath, the cooled sheathed yarn is taken up (also not shown). The water bath can be eliminated by providing an air gap sufficient in length to cool the sheathed yarn to below the melting point of the polymer melt; the yarn runs through the cooling zone (air gap) to a pair of rubber covered nip rolls to be taken up. If the option of stretching the core yarn simultaneous with sheathing is desired, a conventional yarn feeding device can be provided, upstream of the crosshead die, with the capability of restraining the yarn against the tension of a take-up device located on the exit side of the crosshead die.

The processing conditions, particularly the melt temperature, pressure, and flow rate, and the yarn velocity are such that the sheath material adheres to the core yarn. Adhesion is generally benefited by higher melt temperatures, pressures and flow rates and lower yarn velocity through the melt. However, it will be recognized that if melt temperature is too high and yarn velocity is too low, the yarn will lose a large proportion of its molecular orientation and strength in the crosshead die. At sufficiently high melt temperature and low yarn velocity, the yarn will melt and sheathing becomes impossible.

Surprisingly, it is found that the requisite combination of adhesion and operability are obtained when the melt temperature of the sheath material is above the melting point of the core yarn. Yarn melting point is determined by Differential Scanning Calorimeter (DSC) at a heating rate of 10° C./min. Preferably the melt temperature is at least about 25° C., more preferably at least about 50° C., above the yarn melting point. As a practical matter, melt temperatures range from about 190° to about 260° C. Melt temperature is measured by means of a thermocouple inserted in the melt stream within or immediately preceding the crosshead die. Pressure of the melt on the core yarn in the crosshead die assists adhesion. It is preferred that the crosshead melt pressure at the melt entrance 30 be at least about 3.4 MPa. It will be understood that the actual pressure of the melt on the core yarn will be somewhat less than measured as a result of pressure drops in the die. Preferred yarn velocities range from about 90 to about 900 meters per minute (m/min), more preferably about 150 to about 600 m/min. The melt is supplied at a melt throughput sufficient to form from about 10 to about 90, more preferably about 15 to about 60, most preferably about 20 to about 45 weight percent of the sheathed core yarn. The preferred melt flow rate, or throughput, ranges from about 0.4 to about 10 kg/hr, more preferably about 2 to about 5 kg/hr. Yarn residence time in die 23 typically ranges from about 0.001 to about 0.10, more preferably about 0.01 to about 0.05, seconds.

Pretreatment of the core yarn to enhance adherence of the melt thereto preferably occurs after twisting just prior to extrusion sheathing. There are several alternate pretreatments available. The surface of the core yarn can be exposed to a high voltage corona or plasma. Greater detail on plasma treatment can be found in Kaplan, S. L. et al., *Gas Plasma Treatment of SPECTRA® Fiber*, SAMPE Quarterly, Vol. 19, No. 4, July 1988, pp. 55–59, hereby incorporated by reference. Additionally or alternatively, the surfaces of the individual fibers of the core yarn can be primed with an effective amount of a resin having ethylene crystallinity and a melting point of less than about 135° C. Preferred primers are PRIMACOR® ethylene-acrylic acid copolymers, grades 5980 and 5990 manufactured by the Dow Chemical Company, and A-C®X-413 ethylene-acrylic acid polyamide graft copolymers manufactured by AlliedSignal, Inc. The primers are preferably applied to the yarn as a dispersion in water and the yarn then dried. Alternatively, the surface of the core yarn can be scoured to remove any residual finish therefrom. As yet another alternative/additional pretreatment, the surface of the core yarn can be wetted with an effective amount of mineral oil to soften or solvate the surface: These two latter pretreatments preferably occur prior to twisting.

The post-stretching step takes place after the sheathed yarn has been cooled. Preferably the sheathed core yarn is post-stretched at least about 50 percent, more preferably at least about 100 percent, at a temperature within about 10° C. of the melting point of the core yarn, at a stretch rate of less than about 1 sec$^{-1}$, and the post-stretched sheathed yarn is cooled under tension sufficient to retain the highly oriented state of the core yarn. By stretch rate is meant the stretching velocity difference divided by the length of the stretching zone. For example if fiber or yarn being stretched is fed to the stretch (draw) zone of ten meters at ten meters per minute (m/min) and withdrawn at a rate of twenty m/min; the stretching rate would be (20 m/min−10 m/min) divided by 10 m which equals one minute$^{-1}$. See U.S. Pat. No. 4,422,993, hereby incorporated by reference, at column 4, lines 26 to 31. Post-stretching is described in greater detail in EP 205 960B. The advantageous properties achieved through post-stretching the sheathed core yarn are higher tenacity, higher tensile modulus, lower ultimate elongation and smoother surface texture.

Figure 3:
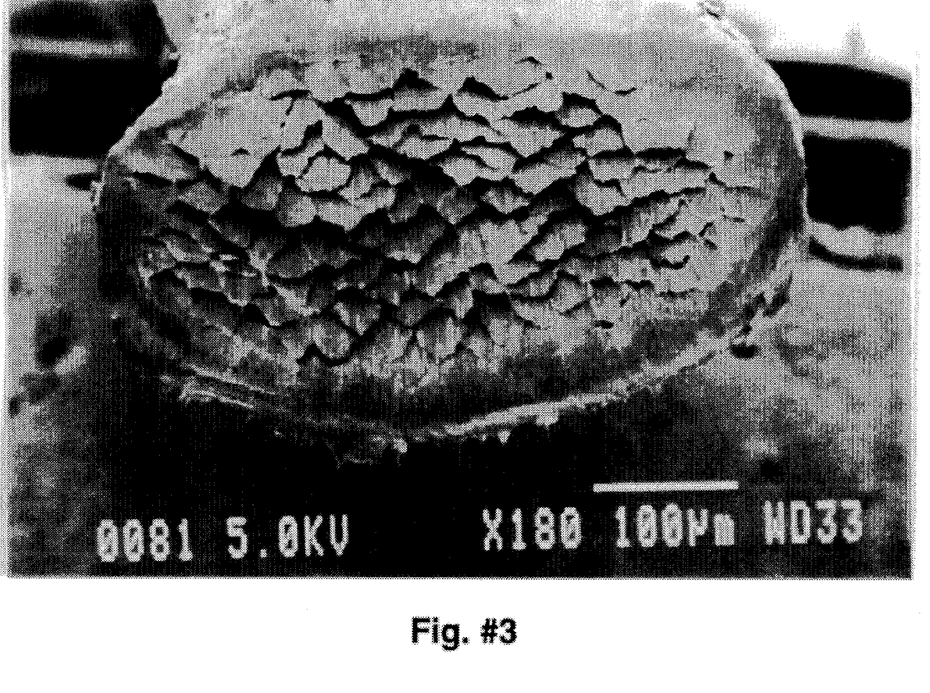
FIG. 3 is a scanning electron micrograph of the cross-section of the quasi monofilament prepared in Example 45.

The quasi monofilament thus prepared consists of the core yarn and a surrounding adherent sheath. Some penetration of the core yarn by the sheath polymer has occurred but the sheath does not fill the interstices of the polyethylene core like "coated" fibers of the prior art. Here, the sheath material is primarily at the surface with some penetration into the core fiber bundle, as illustrated in FIG. 3. In the prior art, the coating completely penetrated the yarn bundle. Thus, at equal deniers of the base yarns and final products, the diameter of the quasi monofilament of the present invention is larger than that of the solution coated yarn bundle of the prior art where the coating would primarily lie in the interstices between filaments.

The invention will be illustrated by the examples and comparative examples which follow. A description of the components of the sheathing compositions evaluated is given in Table I.

Comparative Examples 1–8

Figure 2:
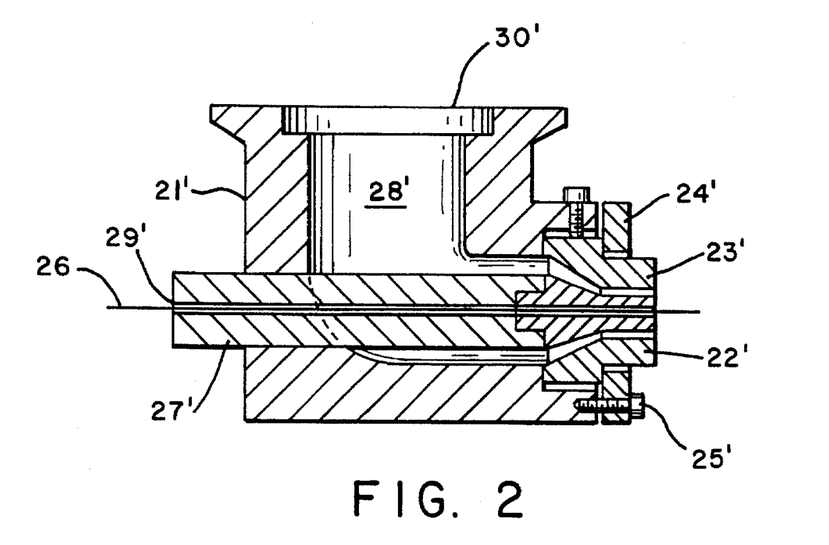
FIG. 2 is a top view in section of apparatus similar to that used in Comparative Examples 1 through 18.

A single screw extruder of 2.54 cm diameter and 25:1 L/D was fitted with a crosshead die of 0.107 cm exit diameter. Polymer feed to the extruder consisted of an ethylene-acrylic acid copolymer containing 19.6 percent acrylic acid available from Dow Chemical under the designation XU-60751.15 (Table I). The polymer had a 270 melt index measured by ASTM D1238 at 125° C./2.16 kg and a tensile strength at yield of 7.58 MPa. The polymer was melted and conveyed by the screw extruder to a crosshead vacuum die similar to that depicted in FIG. 2, which is found in the Handbook of Plastic Materials and Technology, p. 1208, John Wiley & Sons, Inc., New York (1990). Parts which correspond to those of FIG. 1, previously described, are designated by the same numeral with a prime. The design of the crosshead die was such that the extruded polymer melt contacted core yarn 26 immediately at the exit of die 23' rather than in the interior of die 23'. A vacuum connection to the interior of die 23' along the yarn path aided in pulling the melt into contact with yarn 26. The pressure of the melt on the core yarn was equal to the vacuum reading as set forth in Table II.

Traversing through the crosshead die in a direction perpendicular to the axis of the extruder was a 60 filament SPECTRA® 900 high strength polyethylene yarn of 650 total denier, commercially available from AlliedSignal, Inc. It was of 28 g/d tenacity, 1200 g/d modulus, 1,300,000 kg/kg-mole molecular weight and possessed a melting point of 147° C.

After contacting the polymer melt at the exit of the crosshead die and passing through an air gap of 20.3 cm, the sheathed yarn was quenched in a water bath. An extrusion sheathed quasi monofilament consisting of the multi-filament core yarn and its polymer sheath was thereby produced. Melt temperatures, yarn take-up speeds, sheathed yarn deniers and sheathing composition content were varied as given in Table II.

Testing of the quasi monofilaments made in these examples showed that the sheaths had poor adhesion to the core yarn, could easily be stripped or abraded from the core yarn and were therefore unsatisfactory.

Comparative Example 9

In Comparative Example 9, a quasi monofilament was prepared in the same manner as described in Example 1 but the sheathing composition was Dow PRIMACOR® 3460 of 20 g/10 min melt index at 190° C./2.16 kg, 9.5 percent acrylic acid content, and 7.34 MPa tensile strength at yield (Table I). Sheath adhesion/abrasion resistance of this sample was somewhat improved but was still unsatisfactory.

Comparative Examples 10–14

In Comparative Examples 10 through 14, quasi monofilaments were prepared in the same manner as described above but the sheathing compositions were 50/50 and 67/33 blends of Dow 60751.15/PRIMACOR 3460 as shown in Table II. The blends were formed by feeding a pellet mixture to the extrusion coating extruder. Weight average tensile strength of the blends was less than 7.4 MPa. In Comparative Example 10 only, the core yarn was an AlliedSignal, Inc., commercially available product, SPECTRA® 1000 polyethylene yarn, of 215 denier, 60 filaments, 33 g/d tenacity, 1500 g/d modulus, 1,300,000 kg/kg-mole molecular weight and 147° C. melting point. Sheath adhesion/abrasion resistance of all samples was unsatisfactory.

Comparative Examples 15–18

In Comparative Examples 15 through 18, quasi monofilaments were prepared in the same manner as described above but the sheathing resins were Tenite 812A low density polyethylene (LDPE) of 7.31 MPa tensile strength or Tenite M2001-P high density polyethylene (HDPE) of 22.06 MPa tensile strength. Sheath adhesion/abrasion resistance of all samples was unsatisfactory (Table II).

Comparative Examples 19–27

The type of crosshead extrusion die was changed to one in which the sheathing composition was brought into contact with the fiber bundle under pressure within the interior of the die as illustrated in FIG. 1 and previously described. The exit diameter of bore 29 at guider tip 22 was 0.046 cm, and the exit diameter from die 23 was 0.061 cm. Tenite M2001-P HDPE was used as the primary polymer resin in Comparative Examples 19 through 22. A blend of Tenite M2001-P and AlliedSignal, Inc., AC-735 polyethylene wax formed the sheathing composition in Comparative Examples 23 through 27. The blends were formed by feeding a pellet mixture to the extrusion coating extruder. Sheath adhesion/abrasion resistance of the quasi monofilaments of these Comparative Examples was slightly improved but still unsatisfactory. Table III shows the conditions under which these Comparative Examples were prepared.

Examples of the Invention 28–33

The quasi monofilaments of Examples 28 through 30 were prepared in the same manner as that of Comparative Example 19 but the sheathing composition was a blend of 72 weight percent Tenite M2001-P, 18 weight percent Paxxon 4261 and 10 weight percent AC-735. The blends were formed by feeding a pellet mixture to the extrusion coating extruder. Sheath adhesion and abrasion resistance of these Examples was satisfactory (Table III). Comparison of these examples with Comparative Examples 23 through 27 shows the benefit of inclusion of 18 weight percent of the low melt index Paxxon 4261 component in the blend. This is an intrinsically tougher, more abrasion resistant component. It will also be noted that, remarkably, melt temperatures in these examples were over 50° C. higher than the melting point of the core yarn, and melt pressures were in excess of 13.0 MPa. Both of these factors aided in adherence of the sheath to the core yarn.

The quasi monofilaments of Examples 31 through 33 were prepared in the same manner as those of Examples 28 through 30 but the sheathing composition included a higher concentration of the low melt index Paxxon 4261 component. The blend contained 54 weight percent Tenite 2001-P, 36 weight percent Paxxon 4261, and 10 weight percent AC-735. Sheath adhesion/abrasion resistance of the sheath to the core yarn was satisfactory (Table III).

Examples of the Invention 34–39

Table IV shows the production conditions for these examples. The core yarn was 60 filament SPECTRA® 900, 650 denier with 0.9 tpi of twist. The compositions of polymer blends SK-1 and SK-2 are given in Table VI. Prior to extrusion coating, the components of the blend were dry blended and fed to a Killion single screw extruder of 2.54 cm nominal diameter with a screw having a 1.4 to 1 extrusion screw compression ratio and a length to diameter ratio of 30 to 1. This material was extruded at a temperature of 233°–239° C. through a 0.318 cm diameter rod die and quenched and pelletized. The quasi monofilaments of these Examples possessed satisfactory sheath adhesion/abrasion resistance.

Following extrusion coating, the yarn from Example 35 was post-stretched to produce the lower denier, higher tenacity sample of Example 36. Post-stretching was conducted in two in-line stages. The first stage stretch was 165 percent at a stretch rate of 0.012 $\sec^{-1}$ at 157° C. The second stage stretch was 15 percent at a stretch rate of 0.009 $\sec^{-1}$ at 159° C. Fiber physicals are set forth in Table VII.

Examples of the Invention 40–44

Table V shows the production conditions for these examples. The core yarn was 60 filament SPECTRA® 900, 650 denier with 5.0 tpi of twist. In Example 42, the yarn was pretreated with 3.5 percent mineral oil. In Example 43, the yarn was pretreated with 6.5 percent of PRIMACOR 5980, melting point 79° C., applied as a water based dispersion and then dried. In Example 44, the yarn was pretreated with 6.8 percent of A-C®X-413, Mettler Drop Point 99°–107° C. (ASTM D3954), similarly applied as a water based dispersion. All percentages are weight percent based on the weight of the untreated yarn. Pretreatment occurred prior to twisting in Example 42; pretreatment occurred after twisting in the other examples.

In Example 40, the polymer blend composition was SK-6. In Examples 41 through 44, the polymer blend composition was SK-9. The composition of polymer blends SK-6 and SK-9 are given in Table VI. Prior to extrusion coating, the components of the blends were dry blended and fed to a compounding extruder having a length to diameter ratio of 30 to 1. The materials were extruded at a temperature of 233°–239° C. through a 0.318 cm diameter rod die and quenched and pelletized.

The quasi monofilaments of Examples 40 through 44 possessed satisfactory sheath adhesion/abrasion resistance. The adhesion/abrasion resistance of the quasi monofilaments of Examples 41 through 44 were greater than that of Example 40, which demonstrates the benefit of the composition of blend SK-9 over that of SK-6 and the benefits of the various pretreatments.

Examples of the Invention 45–55

Table V also shows the production conditions for these examples. The core yarn was a 120 filament SPECTRA® 1000 high strength polyethylene yarn of 430 total denier, nominally 36.5 g/d tenacity, 1400 g/d nodulus, 1,300,000 kg/kg-mole molecular weight, melting point about 147° C., with 5.0 tpi of twist. The exit diameter of bore 29 at guider tip 22 was 0.038 cm, and the exit diameter from die 23 was 0.046 cm. The length of the air gap was increased to vary from about 165 to 432 cm. The core yarn in Example 45 received no pretreatment. The core yarn in Example 46 received plasma treatment. Examples 49, 51 and 52 received corona treatment. In Example 49, the corona treatment was followed by application of 5.7% A-C®X-413. In Example 51, the corona treatment was followed by application of 5.0% PRIMACOR 5980. In Examples 47 and 48, the core yarns received applications of A-C®X-413 or PRIMACOR 5980 without prior corona treatment. In Example 50, the core yarn was scoured prior to twisting to remove finish oils applied during yarn manufacture. The yarn in Examples 53–55 received no pretreatment but the air gap was increased in these Examples from 165 cm to 229 cm to 432 cm, respectively, with elimination of the water bath in Example 55. In all of these examples, the polymer blend composition was SK-9.

The plasma treatment of Example 46 utilized a PS1010 continuous reactor, available from Airco, Plasma Science Division. Conditions were as follows: 300 watts power, 1 minute residence time, 0.5 tort pressure, with mixtures of oxygen and gaseous fluorocarbons.

The corona treatment of Examples 49, 51 and 52 utilized a double-sided corona treater, model CMD-150-MMS, with two corona generators, model SOA-150, commercially available from Softal of America, Incorporated, of Pawtucket, R.I. Conditions were as follows: 0.6 kilowatts on each generator, 0.35 to 0.45 mil gap for twisted core yarn to pass through, and line speed of about 12.2 m/m.

The scouring in Example 50 took place as follows. An end of yarn was run through a first water bath at ambient temperature until wetted out. The yarn was then passed through a second water bath containing 0.1 g/liter of a nonionic surfactant, Hostapur CX, 0.5 g/liter of trisodium phosphate, and a sufficient amount of sodium hydroxide to bring the pH of the bath to about 9.0–9.5, at a temperature of 49° C. The yarn was then passed through two rinse baths at 49° C. and 27° C., respectively. The rinsed yarn was rolled into a bundle and dried at about 100° C. in a vacuum oven.

The quasi monofilaments produced in Examples 45–55 possessed satisfactory sheath adhesion/abrasion resistance. The adhesion/abrasion resistances of the products of Examples 46–51 were equal to or greater than that of product from Example 45, which demonstrates the benefit of the various pretreatments. The adhesion/abrasion resistance of the product of Example 45 was superior to that of product from Example 41, and the adhesion/abrasion resistances of quasi monofilaments produced in Examples 54 and 55 were superior to that produced by Example 45, which demonstrates the benefit of a longer air gap.

FIG. 3 is a scanning electron micrograph of the cross-section of the sheathed quasi monofilament prepared in Example 45. This is illustrative of the sheath-core structure of the quasi monofilaments made by the process of this invention. No primer was used in Example 45. It will be recognized that application of a primer will tend to fill in the spaces between the inner filaments but that the sheath material will still constitute an annular ring surrounding and penetrating the spaces between the outer layers of the core yarn.

TABLE I

Properties of Materials in Extrusion Coating Trials

| Designation | Description | Density, g/cm³ | Melt Index, g/10 min | Tensile Strength at Yield, MPa | Brookfield Viscosity @ 140° C. |
|---|---|---|---|---|---|
| Dow XU60751.15 | Ethylene-Acrylic Acid Copolymer | 0.91 | 270* | <7.6 | |
| Dow 3460 | Ethylene-Acrylic Acid Copolymer | 0.938 | 20 | 7.3 | |
| Tenite 812A | Low Density Polyethylene | 0.92 | 200 | 7.3 | |
| Tenite E 6838-065 | Low Density Polyethylene | 0.92 | 35 | 8.3 | |
| Tenite M2001-P | High Density Polyethylene | 0.953 | 11.5 | 22.1 | |
| Paxxon 4261 | High Density Polyethylene | 0.946 | <0.1 | 23.4 | |
| Paxxon 5261 | High Density Polyethylene | 0.953 | <0.1 | 26.9 | |
| Sclair 2915 | High Density Polyethylene | 0.959 | 65 | 29.0 | |
| AC Polyethylene 735 | Polyethylene Wax | 0.921 | >1000 | <6.9 | 5500–6500 cps |
| AC Polyethylene 6 | Polyethylene Wax | 0.92 | >1000 | <6.9 | 375 cps |

ASTM Method
D792
D1238 at 190° C./2.16 kg; *125° C./2.16 kg
D638

TABLE II

COMPARATIVE EXAMPLES

| Comparative Example No. | Core Yarn | Coating Material | Wt. Avg. Tensile Strgth. MPa | Melt Temp., C. | Vacuum | Air Gap, cm. | Takeup m/min | Thruput, g/min | Residence Time, sec. | Denier | % Coating | Adhesion/ Abrasion |
|---|---|---|---|---|---|---|---|---|---|---|---|---|
| 1 | S900/650 | Dow XU-60751.15 | <7.6 | 182 | 12.7 cm Hg | 13 | 320 | 10.1 | 0.029 | 935 | 30 | Unsat. |
| 2 | | Dow XU-60751.15 | <7.6 | | " | " | 198 | | 0.046 | | | |
| 3 | | Dow XU-60751.15 | <7.6 | 182 | " | " | 198 | | 0.046 | | | Unsat. |
| 4 | | Dow XU-60751.15 | <7.6 | 182 | " | " | 198 | 25.3 | 0.046 | 1801 | 64 | Unsat. |
| 5 | | Dow XU-60751.15 | <7.6 | 182 | " | " | 198 | 26.4 | 0.046 | 1850 | 65 | Unsat. |
| 6 | | Dow XU-60751.15 | <7.6 | 196 | " | " | 198 | | 0.046 | | | Unsat. |
| 7 | | Dow XU-60751.15 | <7.6 | 196 | " | " | 175 | 20.0 | 0.052 | 1679 | 61 | Unsat. |
| 8 | | Dow XU-60751.15 | <7.6 | 191 | " | " | 137 | | 0.067 | | | Unsat. |
| 9 | | Dow 3460 | 7.3 | 191 | " | " | 137 | | 0.067 | | | Unsat. |
| 10 | S1000/215 | 50/50 Blend | <7.4 | 196 | " | " | 177 | 72.7 | 0.052 | 4351 | 95 | Unsat. |
| 11 | S900/650 | 50/50 Blend | <7.4 | 196 | " | 10 | 178 | 107.5 | 0.051 | 6077 | 89 | Unsat. |
| 12 | | 50/50 Blend | <7.4 | 199 | " | 10 | 175 | 35.5 | 0.052 | 2473 | 74 | Unsat. |
| 13 | | 67/33 Blend | <7.4 | 216 | " | 10 | 178 | 97.5 | 0.051 | 5568 | 88 | Unsat. |
| 14 | | Blend | <7.4 | 218 | " | 5 | 178 | 33.7 | 0.051 | 2350 | 72 | Unsat. |
| 15 | S900/650 | Tenite 812A | 7.3 / 7.3 | 169 | " | 8 | 187 | | 0.049 | | 50 | Unsat. |
| 16 | | Tenite 812A | 7.3 | 166 | " | 8 | 187 | | 0.049 | | 56 | Unsat. |
| 17 | | Tenite 6838-065 | 8.3 | 188 | " | 8 | 93 | | 0.098 | | 76 | Unsat. |
| 18 | | Tenite M2001-P | 22.1 | 207 | 16 | 8 | 123 | | 0.074 | | 62 | Unsat. |

TABLE III

COMPARATIVE EXAMPLES (Continued)

| Comparative Example No. | Core Yarn | Coating Material | Wt. Avg. Tensile Strgth. MPa | Melt Temp., C. | Melt Press. MPa | Air Gap, cm | Takeup m/min | Thru-put, g/min | Residence Time, sec. | Denier | % Coating | Adhesion/Abrasion |
|---|---|---|---|---|---|---|---|---|---|---|---|---|
| 19 | S900/650 | Tenite | 22.1 | 207 | 9.24 | 20 | 184 | 27.0 | 0.050 | 1970 | 67 | Unsat. |
| 20 | | M2001-P | 22.1 | 218 | 10.00 | 10 | 184 | 25.8 | 0.050 | 1912 | 66 | Unsat. |
| 21 | | " | 22.1 | 224 | 10.83 | 5 | 182 | | 0.050 | | | Unsat. |
| 22 | | " | 22.1 | 224 | 10.83 | 5 | 182 | | 0.050 | | | Unsat. |
| 23 | | 90 Wt % M2001-P | 20 | 223 | 7.86 | 5 | 202 | 24.9 | 0.045 | 1757 | 63 | Unsat. |
| 24 | | 10 Wt % AC-735 | 20 | 224 | 6.90 | 5 | 204 | | 0.045 | | | Unsat. |
| 25 | | " | 20 | 233 | 6.90 | 5 | 206 | | 0.044 | | | Unsat. |
| 26 | | " | 20 | 234 | 6.90 | 5 | 207 | | 0.044 | | | Unsat. |
| 27 | | " | 20 | 234 | 6.90 | 5 | 207 | | 0.044 | | | Unsat. |

TABLE IV

EXAMPLES OF THE INVENTION

| Example No. | Core Yarn | Coating Material | Wt. Avg. Tensile Strgth. MPa | Melt Temp., C. | Melt Press., MPa | Air Gap, cm | Takeup m/min | Thru-put, g/min | Residence Time, sec. | Denier | % Coating | Adhesion/Abrasion |
|---|---|---|---|---|---|---|---|---|---|---|---|---|
| 28 | S900/650 | 72 Wt % M2001-P | 21 | 235 | 16.07 | 5 | 212 | | 0.043 | | | Satisfactory |
| 29 | " | 18 Wt % Paxxon 4261 | 21 | 235 | 13.31 | 5 | 213 | 18.8 | 0.043 | 1442 | 55 | Satisfactory |
| 30 | " | 10 Wt % AC-735 | 21 | 235 | 13.51 | 5 | 188 | 21.3 | 0.049 | 1670 | 60 | Satisfactory |
| 31 | " | 54 Wt % M2001-P | 21 | 238 | 27.58 | 5 | 188 | 20.6 | 0.049 | 1638 | 60 | Satisfactory |
| 32 | " | 36 Wt % Paxxon 4261 | 21 | 235 | 26.20 | 5 | 215 | 20.3 | 0.043 | 1500 | 56 | Satisfactory |
| 33 | 0.9 tpi | 10 Wt % AC-735 | 21 | 235 | 22.75 | 5 | 219 | | 0.042 | | | Satisfactory |
| 34 | " | SK-1 | 21 | 232 | 18.75 | 5 | 283 | 15.5 | 0.032 | 1143 | 43 | Satisfactory |
| 35 | " | " | 21 | 232 | 16.89 | 5 | 410 | 16.7 | 0.022 | 1017 | 36 | Satisfactory |
| 36 | | | | | | RESTRETCHED | | | | 319 | 36 | Satisfactory |
| 37 | " | 50/50 SK1/SK2 | 21 | 243 | 28.06 | 5 | 306 | 13.5 | 0.030 | 1048 | 38 | Satisfactory |
| 38 | " | 50/50 SK1/SK2 | 21 | 249 | 26.48 | 5 | 265 | 10.3 | 0.035 | 1001 | 35 | Satisfactory |
| 39 | " | 50/50 SK1/SK2 | 21 | 249 | 24.34 | 5 | 416 | 10.2 | 0.022 | 871 | 25 | Satisfactory |

TABLE V

| Example No. | Core Yarn | Pretreatment/Precoat | Twist | Coating Material | Wt. Avg. Tens. Strength, MPa | Melt Temp., C. | Melt Press. MPa | Air Gap cm | Takup m/min | Thru-put g/min | Residence Time, sec | Denier | % Coating | Adhesion/Abrasion |
|---|---|---|---|---|---|---|---|---|---|---|---|---|---|---|
| 40 | S900/650 | None | 5 tpi | SK-6 | 21 | 238 | 5.9 | 26.7 | 210 | 8.5 | 0.044 | 1016 | 36 | Satisfactory |
| 41 | S900/650 | None | 5 tpi | SK-9 | 28 | 238 | 11.5 | 26.7 | 206 | 8.6 | 0.044 | 1026 | 37 | Satisfactory |
| 42 | S900/650 | 3.5% Mineral Oil | 5 tpi | SK-9 | 28 | 249 | 10.7 | 26.7 | 207 | 8.7 | 0.044 | 1026 | 37 | Satisfactory |
| 43 | S900/650 | 6.5% Primacor 5980 | 5 tpi | SK-9 | 28 | 236 | 10.7 | 26.7 | 208 | 9.5 | 0.044 | 1061 | 39 | Satisfactory |

TABLE V-continued

| Example No. | Core Yarn | Pretreatment/ Precoat | Twist | Coating Material | Wt. Avg. Tens. Strength, MPa | Melt Temp., C. | Melt Press. MPa | Air Gap, cm | Takup m/min | Thruput g/min | Residence Time, sec | Denier | % Coating | Adhesion/ Abrasion |
|---|---|---|---|---|---|---|---|---|---|---|---|---|---|---|
| 44 | S900/650 | 6.8% ACX-413 | 5 tpi | SK-9 | 28 | 243 | 10.0 | 26.7 | 204 | 9.3 | 0.045 | 1059 | 39 | Satisfactory |
| 45 | S1000/430 | None | 5 tpi | SK-9 | 28 | 238 | 13.8 | 165 | 203 | 6.3 | 0.045 | 711 | 40 | Satisfactory |
| 46 | S1000/430 | Plasma | 5 tpi | SK-9 | 28 | 252 | 13.0 | 165 | 203 | 5.8 | 0.045 | 686 | 37 | Satisfactory |
| 47 | S1000/430 | 5.7% ACX-413 | 5 tpi | SK-9 | 28 | 252 | 12.9 | 165 | 203 | 6.8 | 0.045 | 732 | 41 | Satisfactory |
| 48 | S1000/430 | 5.0% Primacor 5980 | 5 tpi | SK-9 | 28 | 241 | 13.5 | 165 | 203 | 6.7 | 0.045 | 727 | 41 | Satisfactory |
| 49 | S1000/430 | Corona + 5.7% ACX-413 | 5 tpi | SK-9 | 28 | 246 | 11.7 | 165 | 203 | 6.6 | 0.045 | 723 | 41 | Satisfactory |
| 50 | S1000/430 | Scoured | 5 tpi | SK-9 | 28 | 243 | 13.2 | 165 | 203 | 6.3 | 0.045 | 710 | 39 | Satisfactory |
| 51 | S1000/430 | Corona + 5% Primacor 5980 | 5 tpi | SK-9 | 28 | 238 | 10.9 | 165 | 202 | 6.2 | 0.045 | 707 | 39 | Satisfactory |
| 52 | S1000/430 | Corona | 5 tpi | SK-9 | 28 | 238 | 15.9 | 165 | 202 | 7.0 | 0.045 | 741 | 42 | Satisfactory |
| 53 | S1000/430 | None | 5 tpi | SK-9 | 28 | 238 | 13.5 | 165 | 202 | 6.8 | 0.045 | 733 | 41 | Satisfactory |
| 54 | S1000/430 | None | 5 tpi | SK-9 | 28 | 238 | 13.5 | 229 | 202 | 7.3 | 0.045 | 753 | 43 | Satisfactory |
| 55 | S1000/430 | None | 5 tpi | SK-9 | 28 | 238 | 13.8 | 432 | 203 | 7.1 | 0.045 | 746 | 42 | Satisfactory |

TABLE VI

COMPOSITIONS OF BLENDS

| Component | Weight Percent of Component In Blend | | | |
|---|---|---|---|---|
| | SK-1 | SK-2 | SK-6 | SK-9 |
| Paxxon 4261 | 36.90 | 73.80 | 36.79 | |
| Paxxon 5261 | | | | 49.47 |
| Sclair 2915 | | | | 49.47 |
| Tenite M2001-P | 55.35 | 18.45 | 55.18 | |
| AC 6 | 7.00 | 7.00 | 7.00 | |
| Irganox 1010 | | | 0.38 | 0.38 |
| Irganox B-225 | 0.74 | 0.74 | | |
| Tinuvin 783 | | | 0.60 | 0.60 |
| Hytherm Blue | 0.01 | 0.01 | 0.023 | |
| Solvent Green #5 | | | 0.023 | |
| Pylakrome Dark Olive | | | | 0.08 |
| | 100.00 | 100.00 | 100.00 | 100.00 |

TABLE VII

Fiber Physicals

| Example | Denier | Tenacity g/d | Tensile Modulus g/d | % U.E. |
|---|---|---|---|---|
| 35 | 1017 | 16 | 489 | 4.5 |
| 36 (post-stretched) | 319 | 20 | 746 | 3.7 |

ASTM Method
D885 strain rate 100% per minute

We claim:

1. A process for making an abrasion resistant quasi monofilament, comprising the steps of:

a. continuously feeding a core polyethylene multi-filament yarn having a tenacity of at least about 15 g/d and a tensile modulus of at least about 500 g/d through a crosshead die, while simultaneously b. supplying a polymer melt at a temperature greater than the melting point of the core yarn to the die, for c. sheathing the core yarn within the die with the melt under a sufficient pressure to cause the melt to adhere to the core yarn; and d. cooling the sheathed yarn to below the melting point of the polymer melt.

2. The process of claim 1 wherein the yarn is fed at a yarn velocity of up to about 900 m/min, the yarn has a residence time in the die of up to about 0.10 sec., and the melt is supplied at a melt throughput sufficient to form from about 10 to about 90 weight percent of the sheathed core yarn.

3. The process of claim 2 wherein the yarn is fed at a yarn velocity of about 150 to about 600 m/min, the yarn has a residence time in the die of about 0.01 to about 0.05 sec., and the melt is supplied at a melt throughput sufficient to form from about 15 to about 60 weight percent of the sheathed core yarn.

4. The process of claim 2 wherein the melt is supplied at a melt throughput sufficient to form from about 20 to about 45 weight percent of the sheathed core yarn.

5. The process of claim 1 wherein the temperature is at least about 25° C. above the melting point of the core yarn and the melt is under a pressure of at least about 3.4 MPa at the melt entrance to the crosshead die.

6. The process of claim 5 wherein the temperature is at least about 50° C. above the melting point of the core yarn.

7. The process of claim 1 additionally comprising the step of twisting the core yarn prior to the feeding step.

8. The process of claim 7 wherein the core yarn is twisted with about 0.1 to about 20 tpi.

9. The process of claim 8 wherein the core yarn is twisted with about 0.5 to 15 tpi.

10. The process of claim 7 additionally comprising the step of post-stretching the sheathed core yarn at a temperature within about 10° C. of the melting point of the core yarn at a rate of less than about 1 sec$^{-1}$.

11. The process of claim 7 additionally comprising the step of pretreating the core yarn prior to the feeding step to enhance adherence of the melt to the core yarn.

12. The process of claim 11 wherein the pretreating step comprises priming the surface of the core yarn with an effective amount of a resin having ethylene crystallinity and a melting point of less than about 135° C.

13. The process of claim 11 wherein the pretreating step comprises priming the surface of the core yarn with an effective amount of mineral oil.

14. The process of claim 11 wherein the pretreating step comprises corona treatment of the core yarn.

15. The process of claim 14 wherein the pretreating step further comprises priming the surface of the core yarn with an effective amount of a resin having ethylene crystallinity and a melting point of less than about 135° C. after corona treatment.

16. The process of claim 11 wherein the pretreating step comprises plasma treatment of the core yarn.

17. The process of claim 11 wherein the pretreating step comprises scouring the core yarn.

18. The process of claim 11 wherein the melt is supplied at a melt throughput sufficient to form from about 15 to about 60 weight percent of the sheathed core yarn, the temperature is at least about 25° C. above the melting point of the core yarn, the pressure is at least about 3.4 MPa at the melt entrance to the crosshead die, and the core yarn is twisted with about 0.1 to about 20 tpi.

19. The process of claim 18 wherein the melt is supplied at a melt throughput sufficient to form from about 20 to about 45 weight percent of the sheathed core yarn, the temperature is at least about 50° C. above the melting point of the core yarn, and the core yarn is twisted with about 0.5 to about 15 tpi.

20. The process of claim 7 wherein the melt is supplied at a melt throughput sufficient to form from about 15 to about 60 weight percent of the sheathed core yearn, the temperature is at least about 25° C. above the melting point of the core yarn, the pressure is at least about 3.4 MPa at the melt entrance to the crosshead die, and the core yarn is twisted with about 0.1 to about 20 tpi.

21. The process of claim 20 wherein the melt is supplied at a melt throughput sufficient to form from about 20 to about 45 weight percent of the sheathed core yarn, the temperature is at least about 50° C. above the melting point of the core yarn, and the core yarn is twisted with about 0.5 to about 15 tpi.

22. The process of claim 1 additionally comprising the step of pretreating the core yarn to enhance adherence of the melt to the core yarn.

* * * * *